United States Patent [19]

Ozawa et al.

[11] Patent Number: 4,992,469

[45] Date of Patent: Feb. 12, 1991

[54] METHOD OF OBTAINING AN ANTIPLATELET EFFECT

[75] Inventors: Takayuki Ozawa; Morimitsu Nishikimi; Hiroshi Suzuki; Yoshiharu Shimomura, all of Nagoya; Isao Yamatsu, Inashiki; Shinya Abe, Inashiki; Kouji Yamada, Inashiki; Tohru Fujimori, Tsukuba; Takanobu Takamura, Nagoya, all of Japan

[73] Assignees: Eisai Co., Ltd., Tokyo; Nagoya University, Nagoya, both of Japan

[21] Appl. No.: 738,936

[22] Filed: May 29, 1985

[30] Foreign Application Priority Data

May 31, 1984 [JP] Japan .................. 59-111555

[51] Int. Cl.$^5$ .............................. A61K 31/20
[52] U.S. Cl. .................. 514/559; 260/413; 514/822; 514/824; 514/870; 552/307
[58] Field of Search .......... 260/396 R, 413; 514/559, 822, 824, 870

[56] References Cited

U.S. PATENT DOCUMENTS 4,388,312 6/1983 Terao et al. ............ 260/396 R
4,436,753 3/1984 Imada et al. ........... 260/396 R
4,526,719 7/1985 Terao et al. ............ 260/396 R

FOREIGN PATENT DOCUMENTS 2055097 6/1983 United Kingdom .

Primary Examiner—Vivian Garner
Attorney, Agent, or Firm—Flynn, Thiel, Boutell & Tanis

[57] ABSTRACT

A quinone derivative of the formula (I):

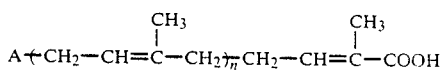

in which A is a group of the formula (IV):

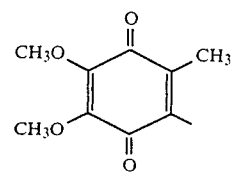

or a group of the formula (V):

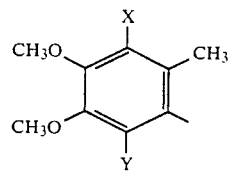

in which X and Y are either the same as or different from each other and each are hydroxy, methoxy or hydrogen; and n is an integer of 1 to 5, is disclosed. The compound is useful as a medicament.

1 Claim, No Drawings

METHOD OF OBTAINING AN ANTIPLATELET EFFECT

The invention relates to a quinone derivative of the formula (I) shown below, a pharmaceutically acceptable salt thereof and a pharmaceutical composition containing the same. The quinone derivative of the invention provides a phospholipase inhibition effect, an antiplatelet effect and a therapeutic and/or preventive effect to a cardiac disease. The invention also relates to use of the quinone derivative for the treatment of the human body by therapy and for the manufacture of a medicament for a therapeutic application. Moreover the invention provides a process for manufacturing the quinone derivative.

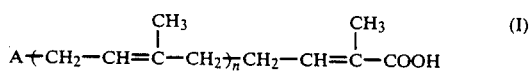

wherein A represents a group of the general formula:

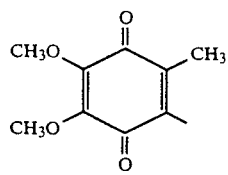

or a group of the general formula:

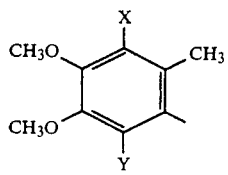

wherein X and Y are the same or different from each other and each represents a hydroxyl or a methoxyl group or a hydrogen atom;
and n represents an integer of 1 to 5.

Ubidecarenone, which is also called coenzyme $Q_{10}$ or ubiquinone$_{10}$, was isolated from mitochondria in bovine cardiac muscle in a crystalline from by Crane et al. in 1957. It widely occurs in vivo, in particular in mitochondria in cells, and is an important constituent of a mitochondrial electron transport system governing energy production.

As a result of our prolonged studies on derivatives of ubidecarenone, we have found that a series of compounds having a carboxyl group at the terminal of the polyprenyl chain in the ubidecarenone molecule would exhibit an excellent physiological activity, thus completing the present invention.

Accordingly the compound of the present invention is a quinone compound having a carboxyl group at the terminal of the polyprenyl chain in the ubidecarenone molecule and represented by the general formula:

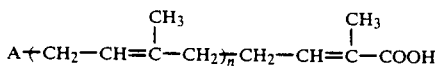

wherein A represents a group of the formula:

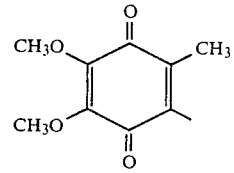

or a group of the formula:

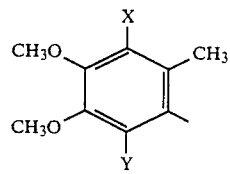

wherein X and Y are the same or different from each other and each represents a hydroxyl or a methoxyl group or a hydrogen atom;
and n represents an integer of 1 to 5.

The compound of the present invention may be prepared by various processes. Typical examples are as follows.

PROCESS 1

In order to prepare a compound of formula (I) wherein A represents a group of the formula:

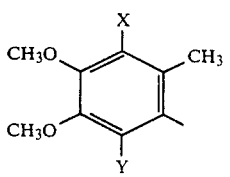

wherein X and Y are the same or different from each other and each represents a hydroxyl or a methoxyl group or a hydrogen atom,
a compound of the formula:

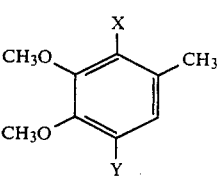

and a compound of the formula:

wherein n represents an integer of 1 to 5;
and R represents a hydrogen atom or a lower alkyl group,
are condensed in the presence of a catalyst such as silica gel/zinc chloride to give one of the aimed compounds (I') of the general formula:

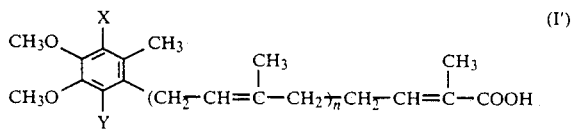

When R in formula (III) represents a lower alkyl group, it may be hydrolyzed with caustic potash or caustic soda to form a carboxylic acid, thus giving compound (I').

PROCESS 2

In order to prepare a compound of formula (I) wherein A represents a group of the formula:

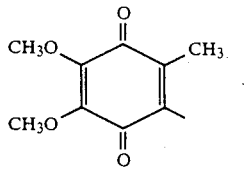

compound (I') of the formula:

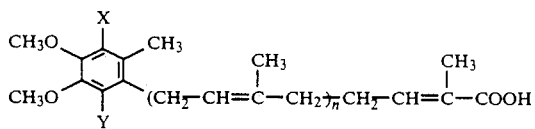

wherein X, Y and n are as defined above; is treated with an oxidizing agent such as ferric oxide or zinc oxide to give a benzoquinone compound (I'') which is one of the aimed compounds and represented by the formula:

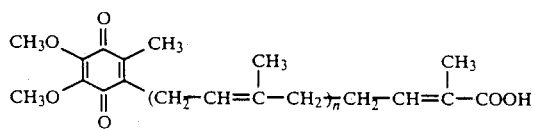

wherein X, Y and n are as defined above.

The compound of the present invention exhibits a remarkably excellent phospholipase inhibition effect as well as an antiplatelet effect, which makes it useful, e.g., as an antiplatelet, a blood compatible agent and a therapeutic agent for various cardiac diseases. More particularly it is available in treating and/or preventing cerebrovascular diseases such as TIA (transient ischemic attack), cerebroinfarct (thrombi and emboli) and cerebral arteriosclerosis; postoperative thrombi, emboli and blood stream disorders accompanying vascular operations and extracorporeal blood circulation; peripheral blood stream disorders caused by emboli or constriction of limb artery such as Buerger's disease, arteriosclerosis obliterans, SLE and Raynaud's disease; congestive failure accompanied by edema, pulmonary congestion or hepatomegaly; and cardiac diseases such as stenocardia and myocardial infarction. The compound of the present invention is further effective in preventing relapse of the foregoing diseases and treating the recuperation thereof.

The compound of the present invention is furthermore effective in treating and/or preventing inflammatory diseases such as various rheumatic diseases.

To further illustrate the effects of the compound of the present invention, the following experimental examples will be given.

EXPERIMENTAL EXAMPLE 1:
PHOSPHOLIPASE $A_2$ INHIBITION EFFECT (1)
Method

Prior to the determination of the activity of phospholipase A by determining myristic acid liberated from a substrate (myristyllecithin) by said enzyme by high-performance liquid chromatography, the following test compounds were added in amounts as shown in Table 1 to examine the effects thereof.

$CoQ_{10}$ was employed for the purpose of comparison.

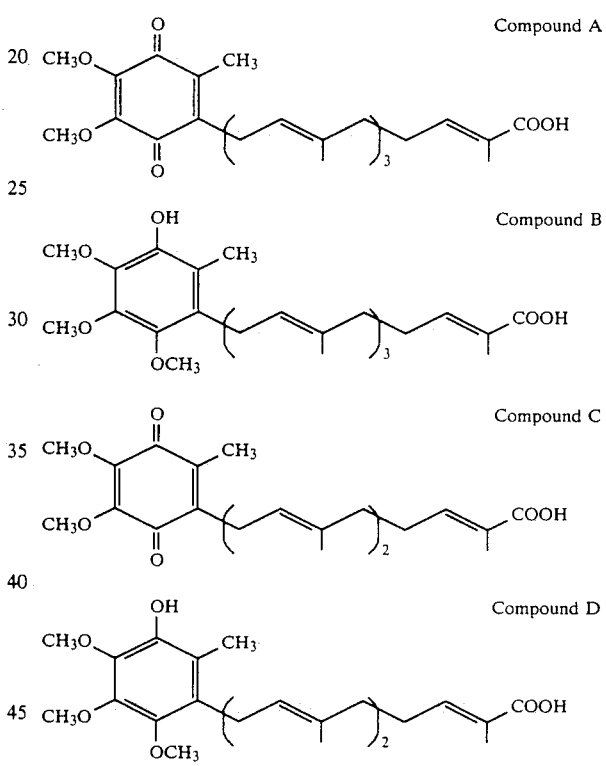

Table 1 shows the result. Each value in Table 1 represents the evaluation of the corresponding compound assuming the value of a physiological saline solution as 100 and indicates the phospholipase $A_2$ inhibition activity thereof.

TABLE 1

| Compound | Final concentration (μM) | Phospholipase A activity (%) |
|---|---|---|
| Compound A | 4 | 66 |
| Compound B | 4 | 55 |
| Compound C | 4 | 25 |
| Compound D | 4 | 24 |
| $CoQ_{10}$ | 43 | 56 |
| Physiological saline solution | — | 100 |

The above table obviously indicates that the compounds of the present invention exert much higher effects of inhibiting phospholipase A than that of $CoQ_{10}$.

EXPERIMENTAL EXAMPLE 2: ANTIPLATELET EFFECT ON HUMAN PLATELETS

Effects of repressing human platelet agglutination of the compounds of the present invention were examined in vitro. Platelet agglutination test was carried out in the following manner with the use of PAF (platelet activating factor; 1-alkyl-2-acetyl-sn-glycero-3-phosphocholine), collagen and ADP as inducers.

(1) Preparation of PRP (Platelet Rich Plasma)

Blood was collected from the venae brachiales of a healthy male adult in an amount of nine parts by volume to one part by volume of a 3.8% sodium citrate solution. The blood was centrifuged at 100 ×g for eight min and PRP separated as the supernatant was collected.

(2) Determination of Platelet Agglutination

To 0.2 ml of the PRP as prepared above, 25 μl portions of test solutions in various concentrations were added and each mixture was incubated at 37° C. for three min. 25 μl of the abovementioned inducer solution was added thereto to induce agglutination. PAF, collagen and ADP were added as inducers to the final concentrations of 100 ng/ml, 1 μg/ml and 5 μM, respectively. Platelet agglutination was determined with an aggregometer (a product of Niko Bioscience Co., Ltd.) by the method of Mustard et al. (cf. Mustard, J.F., Hegaldt, B., Rosewell, H.C., MacMillan, R.C., J. Lab. Clin. Med., 64, 548–559 (1964)). The repressing effect of each test compound was evaluated as the repression ratio with the use of PRP containing vehicle as control.

(3) The following compounds were tested. Compounds A to D are as defined in Experimental Example 1.

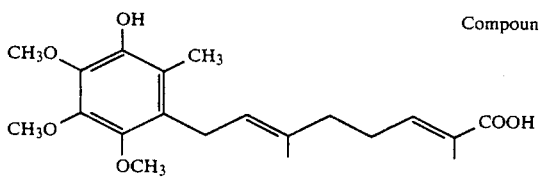

Compound E

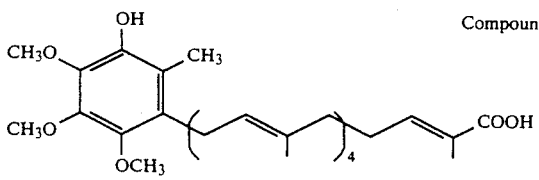

Compound F

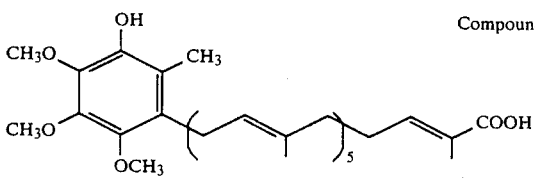

Compound G

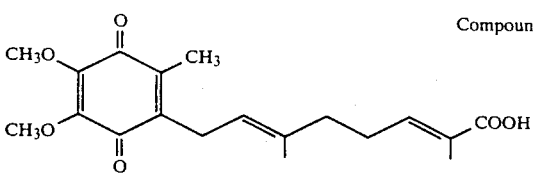

Compound H

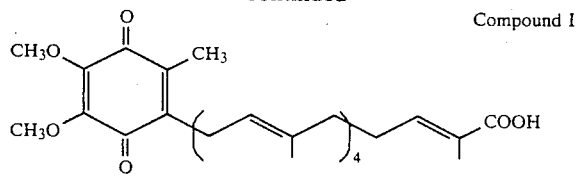

Compound I

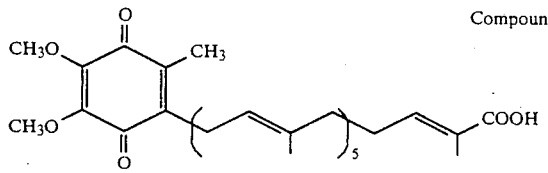

Compound J (4) Table 2 shows the result.

Each figure in Table 2 represents the repression ratio (%) of the corresponding compound.

Table 2 obviously indicates that the compounds of the present invention exert better antiplatelet effects than $CoQ_{10}$.

TABLE 2

| Compound | Concentration (μM) | PAF (%) | Collagen (%) | ADP (%) |
|---|---|---|---|---|
| Compound A | 20 | 27.8 | 62.4 | 12.4 |
| | 50 | 36.0 | | 2.1 |
| | 100 | 42.6 | 86.6 | 22.1 |
| | 200 | 52.9 | | 23.1 |
| Compound B | 20 | 21.6 | 21.4 | 12.9 |
| | 50 | 36.8 | | 24.8 |
| | 100 | 38.4 | 69.6 | 21.5 |
| | 200 | 51.6 | | 24.2 |
| Compound C | 20 | 3.5 | 3.2 | |
| | 50 | 3.4 | | |
| | 100 | 12.2 | 17.2 | |
| | 200 | 47.3 | | 18.3 |
| Compound D | 20 | 4.5 | 2.8 | |
| | 50 | 23.8 | | 9.0 |
| | 100 | 26.0 | 39.3 | 13.5 |
| | 200 | 51.5 | | 21.3 |
| Compound E | 20 | 3.03 | 45.4 | |
| | 50 | 28.1 | | |
| | 100 | 32.5 | 75.8 | 10.7 |
| | 200 | 45.4 | | 23.0 |
| Compound F | 20 | | 5.0 | |
| | 50 | 5.9 | | |
| | 100 | 9.3 | 15.8 | 6.7 |
| | 200 | 49.0 | | 26.3 |
| Compound G | 20 | | | |
| | 50 | 8.1 | | |
| | 100 | 12.8 | 30.2 | 14.0 |
| | 200 | 59.8 | | 23.1 |
| Compound H | 20 | 8.8 | 38.1 | |
| | 50 | 28.2 | | |
| | 100 | 37.8 | 84.3 | 8.8 |
| | 200 | 47.3 | | 18.2 |
| Compound I | 20 | 2.8 | | |
| | 50 | 3.9 | | |
| | 100 | 10.8 | 24.1 | 3.9 |
| | 200 | 53.3 | | 22.0 |
| Compound J | 20 | 6.0 | | |
| | 50 | 2.7 | | 16.5 |
| | 100 | 24.9 | 22.0 | 27.1 |
| | 200 | 65.3 | | 30.1 |
| $CoQ_{10}$ | 20 | 8.0 | 6.5 | |
| | 50 | | | |
| | 100 | 16.2 | 18.7 | 8.7 |
| | 200 | 19.0 | | 11.3 |

To further illustrate the present invention and not by way of limitation, the following examples will be given.

EXAMPLE 1:
6-(7-CARBOXY-3-METHYL-2,6-OCTADIENYL)-2,3,4-TRIMETHOXY-5-METHYLPHENOL 5 g of 2,3,4-trimethoxy-5-methylphenol was dissolved in 10 ml of benzene and 10 g of silica alumina was added thereto. 1.8 g of 8-hydroxy-2,6-dimethyl-2,6-octadienoic acid dissolved in 4 ml of benzene was added to the above solution. The obtained solution was heated to 40° to 50° C. for two hours to allow reaction. The reaction mixture was then filtered and the precipitate was washed with ethyl ether while the filtrate was washed with water, dried over anhydrous magnesium sulfate and concentrated. The concentrate was purified by silica gel chromatography with the use of ether/n-hexane as the eluent to give 1.3 g of the title compound as a colorless oil.

EXAMPLE 2:
6-(11-CARBOXY-3,7-DIMETHYL-2,6,10-DODECATRIENYL)-2,3,4-TRIMETHOXY-5-METHYLPHENOL 5 g of 2,3,4-trimethoxy-5-methylphenol was dissolved in 10 ml of benzene and 6 g of silica gel (Wako gel C-200) and 3 g of zinc chloride were added thereto. 2.4 g of ethyl 2-hydroxy-2,6,10-trimethyl-2,6,10-dodecatrienoate dissolved in 5 ml of benzene was added to the above solution. After reacting at room temperature for 30 min, the reaction mixture was filtered and the precipitate was washed with ethyl ether while the filtrate was washed with water, dried over anhydrous magnesium sulfate and concentrated. The concentrate was dissolved in 50 ml of ethanol and 3 g of caustic soda was added thereto. After refluxing for 30 min, the reaction mixture was poured into diluted hydrochloric acid and extracted with ethyl acetate. The extract was washed with water, dried over magnesium sulfate, concentrated and purified with silica gel chromatography with the use of ethyl acetate/benzene as the eluent to give 1.7 g of the title compound as a colorless oil.

EXAMPLE 3:
6-(15-CARBOXY-3,7,11-TRIMETHYL-2,6,10,14-HEXADECATETRAENYL)-2,3,4-TRIMETHOXY-5-METHYLPHENOL 5 g of 2,3,4-trimethoxy-5-methylphenol was dissolved in 10 ml of benzene and 6 g of silica gel (Wako gel C-200) and 3 g of zinc chloride were added thereto. 3 g of 16-hydroxy-2,6,10,14-tetramethyl-2,6,10,14-hexadecatetraenoic acid dissolved in 5 ml of benzene was added to the above solution. After reacting at room temperature for 30 min, the reaction mixture was filtered and the precipitate was washed with ethyl ether while the filtrate was washed with water, dried over magnesium sulfate anhydride and concentrated. The concentrate was purified by means of silica gel chromatography with the use of ether/n-hexane as the eluent to give 2.1 g of the title compound as a colorless oil.

EXAMPLE 4:
6-(19-CARBOXY-3,7,11,15-TETRAMETHYL-2,6,10,14,18-EICOSAPENTAENYL)-2,3,4-TRIMETHOXY-5-METHYLPHENOL

The procedures of Example 1 were repeated except that 5 g of 2,3,4-trimethoxy-5-methylphenol and 3.2 g of 20-hydroxy-2,6,10,14,18-pentamethyl-2,6,10,14,18-eicosapentaenoic acid were employed as the starting materials to give 2.8 g of the title compound as a colorless oil.

EXAMPLE 5:
6-(23-CARBOXY-3,7,11,15,19-PENTAMETHYL-2,6,10,14,18,22-TETRACOSAHEXAENYL)-2,3,4-TRIMETHOXY-5-METHYLPHENOL

The procedures of Example 1 were repeated except that 5 g of 2,3,4-trimethoxy-5-methylphenol and 3.5 g of 24-hydroxy-2,6,10,14,18,22-hexamethyl-2,6,10,14,18,22-tetracosahexaenoic acid were employed as the starting materials to give 2.5 g of the title compound as a colorless oil.

EXAMPLE 6:
6-(7-CARBOXY-3-METHYL-2,6-OCTADIENYL)-2,3-DIMETHOXY-5-METHYL-1,4-BENZOQUINONE 2 g of 6-(7-carboxy-3-methyl-2,6-octadienyl)-2,3,4-trimethoxy-5-methylphenol as prepared in Example 1 was dissolved in 20 ml of ethyl acetate and 5 g of ferric chloride hexahydrate was added thereto. The reaction mixture was stirred at room temperature for 30 min. After adding 100 ml of ether, it was washed with water, dried over anhydrous magnesium sulfate and concentrated. The concentrate was purified by means of silica gel chromatography with the use of ethyl acetate/benzene as the eluent to give 1.8 g of the title compound as an orange oil.

EXAMPLE 7:
6-(11-CARBOXY-3,7-DIMETHYL-2,6,10-DODECATRIENYL)-2,3-DIMETHOXY-5-METHYL-1,4-BENZOQUINONE

The procedures of Example 6 were repeated except that 1.5 g of 6-(11-carboxy-3,7-dimethyl-2,6,10-dodecatrienyl)-2,3,4-trimethoxy-5-methylphenol as prepared in Example 2 was employed as the starting material to give 1.4 g of the title compound as an orange oil.

EXAMPLE 8:
6-(15-CARBOXY-3,7,11-TRIMETHYL-2,6,10,14-HEXADECATETRAENYL)-2,3-DIMETHOXY-5-METHYL-1,4-BENZOQUINONE

The procedures of Example 6 were repeated except that 2 g of 6-(15-carboxy-3,7,11-trimethyl-2,6,10,14-hexadecatetraenyl)-2,3,4-trimethoxy-5-methylphenol was employed as the starting material to give 1.7 g of the title compound as an orange oil.

EXAMPLE 9:
6-(19-CARBOXY-3,7,11,15-TETRAMETHYL-2,6,10,14,18-EICOSAPENTAENYL)-2,3-DIMETHOXY-5-METHYL-1,4,-BENZOQUINONE

The procedures of Example 6 were repeated except that 2.5 g of 6-(19-carboxy-3,7,11,15-tetramethyl-2,6,10,14,18-eicosapentaenyl)-2,3,4-trimethoxy-5-methylphenol was employed as the starting material to give 2.2 g of the title compound as an orange substance.

EXAMPLE 10:
6-(23-CARBOXY-3,7,11,15,19-PENTAMETHYL-2,6,10,14,18,22-TETRACOSAHEXAENYL)-2,3-DIMETHOXY-5-METHYL-1,4-BENZOQUINONE

The procedures of Example 6 were repeated except that 1.3 g of 6-(23-carboxy-3,7,11,15,19-pentamethyl-2,6,10,14,18,22-tetracosahexaenyl)-2,3,4-trimethoxy-5- methylphenol was employed as the starting material to give 1.1 g of the title compound as an orange substance.

Table 3 shows physicochemical properties of the compounds of the present invention as prepared in Examples 1 to 5 while Table 4 shows those as prepared in Examples 6 to 10.

25 to 30 g in body weight to thereby examine the acute toxicity thereof. Consequently each compound showed $LD_{50}$ of at least 500 mg/kg. The compounds A to J of the present invention were injected into the tail veins of 10 mice as described above in doses of 10, 30, and 100 mg/kg. The mice showed a survival ratio of 100% (i.e. 10/10) in each case, which suggests that the $LD_{50}$ of each compound is at least 100 mg/kg.

TABLE 3

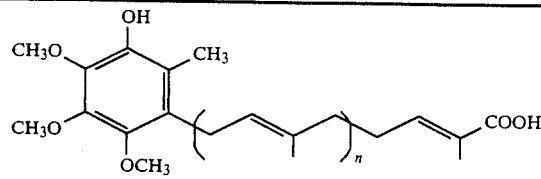

| Example | n | Mol. form. Mol. wt. | Elementary analysis upper; calcd. lower; found C (%) | H (%) | Mass (M+) | NMR (in CDCl₃, TMS): δ (ppm) |
|---|---|---|---|---|---|---|
| 1 | 1 | $C_{20}H_{28}O_6$ 364.42 | 65.91 65.87 | 7.74 7.75 | 364 | 1.78(s,3H),1.82(s,3H),1.96~2.35(m,4H),2.13(s,3H),3.32(d,2H, J=8Hz),3.76(s,3H),3.91(s,3H),3.93(s,3H),5.08(t,1H,J=8Hz), 5.70(bs,1H),6.85(t,1H,J=8Hz),10.40(bs,1H) |
| 2 | 2 | $C_{25}H_{36}O_6$ 432.54 | 69.41 69.43 | 8.39 8.39 | 432 | 1.58(s,3H),1.78(s,3H),1.83(s,3H),1.96~2.35(m,8H),2.13(s,3H), 3.32(d,2H,J=8Hz),3.76(s,3H),3.91(s,3H),3.93(s,3H),5.04(t,1H,J= 8Hz),5.11(t,1H,J=8Hz),5.62(bs,1H),6.85(t,1H,J=8Hz),10.80(bs,1H) |
| 3 | 3 | $C_{30}H_{44}O_6$ 500.65 | 71.97 71.93 | 8.86 8.89 | 500 | 1.57(s,3H),1.59(s,3H),1.77(s,3H),1.83(s,3H),1.90~2.35(m,12H), 2.13(s,3H),3.32(d,2H,J=8Hz),3.76(s,3H),3.91(s,3H),3.93(s,3H), 5.03(t,1H,J=8Hz),5.03(t,1H,J=8Hz),5.13(t,1H,J=8Hz),5.60(bs,1H), 6.85(t,1H,J=8Hz),10.93(bs,1H) |
| 4 | 4 | $C_{35}H_{52}O_6$ 568.77 | 73.91 73.93 | 9.22 9.20 | 568 | 1.57(s,3H),1.59(s,3H),1.61(s,3H),1.78(s,3H),1.83(s,3H),1.90~2.35 (m,H),2.13(s,3H),3.32(d,2H,J=8Hz),3.76(s,3H),3.91(s,3H),3.93(s, 3H),5.03~5.18(m,4H),5.65(bs,1H),6.85(t,1H,J=8Hz),11.05(bs, 1H) |
| 5 | 5 | $C_{40}H_{60}O_6$ 636.88 | 75.43 75.40 | 9.50 9.51 | 636 | 1.57(s,3H),1.59(s,6H),1.61(s,3H),1.98(s,3H),1.83(s,3H),1.90~2.35 (m,20H),2.13(s,3H),3.32(d,2H,J=8Hz),3.76(s,3H),3.91(s,3H),3.93 (s,3H),5.03~5.18(m,5H),5.80(bs,1H),6.85(t,1H,J=8Hz),11.35(bs, 1H) |

TABLE 4

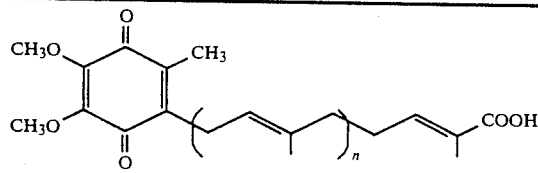

| Example | n | Mol. form. Mol. wt. | Elementary analysis upper; calcd. lower; found C (%) | H (%) | Mass (M+) | NMR (in CDCl₃, TMS): δ (ppm) |
|---|---|---|---|---|---|---|
| 6 | 1 | $C_{19}H_{24}O_6$ 348.38 | 65.50 65.52 | 6.94 6.93 | 348 | 1.76(s,3H),1.82(s,3H),2.05~2.35(m,4H),3.18(d,2H,J=8Hz),3.98 (s,3H),4.00(s,3H),4.97(t,1H,J=8Hz),6.81(t,1H,J=8Hz) |
| 7 | 2 | $C_{24}H_{32}O_6$ 416.50 | 69.21 69.20 | 7.74 7.76 | 416 | 1.58(s,3H),1.74(s,3H),1.84(s,3H),1.93~2.34(m,8H),2.01(s,3H), 3.18(d,2H,J=8Hz),3.98(s,3H),4.00(s,3H),4.94(t,1H,J=8Hz),5.09 (t,1H,J=8Hz),6.87(t,1H,J=8Hz),11.05(bs,1H) |
| 8 | 3 | $C_{29}H_{40}O_6$ 484.61 | 71.87 71.89 | 8.32 8.33 | 484 | 1.58(s,3H),1.61(s,3H),1.74(s,3H),1.84(s,3H),1.93~2.34(m,12H), 2.01(s,3H),3.18(d,2H,J=8Hz),3.98(s,3H),4.00(s,3H),4.94(t,1H,J= 8Hz),5.07(t,1H,J=8Hz),5.13(t,1H,J=8Hz),6.87(t,1H,J=8Hz), 11.30(bs,1H) |
| 9 | 4 | $C_{34}H_{48}O_6$ 552.72 | 73.88 73.86 | 8.75 8.75 | 552 | 1.56(s,3H),1.58(s,3H),1.61(s,3H),1.74(s,3H),1.84(s,3H),1.93~ 2.34(m,16H),2.01(s,3H),3.18(d,2H,J=8Hz),3.98(s,3H),4.00(s,3H), 4.94(t,1H,J=8Hz),5.03~5.18(m,3H),6.87(t,1H,J=8Hz),11.80(bs, 1H) |
| 10 | 5 | $C_{39}H_{56}O_6$ 620.84 | 75.44 75.44 | 9.09 9.08 | 620 | 1.56(s,3H),1.58(s,6H),1.61(s,3H),1.74(s,3H),1.84(s,3H),1.93~ 2.34(m,20H),2.01(s,3H),3.18(d,2H,J=8Hz),3.98(s,3H),4.00(s,3H), 4.94(t,1H,J=8Hz),5.03~5.18(m,4H),6.87(t,1H,J=8Hz),10.50(bs, 1H) |

The toxicity of the compounds of the present invention will be described hereinbelow.

Toxicity Test

The compounds A to J of the present invention were orally administered to male ddY mice of approximately The compound of the present invention exhibits a phospholipase inhibition effect as well as an anti-platelet effect and may be formulated into drugs such as an antiplatelet, a blood compatible agent and a therapeutic and/or preventive agent for cardiac diseases or inflammatory diseases including rheumatic diseases for oral or parenteral, e.g. intramuscular, hypodermical or intravenous administration or as a suppository. The compounds may be administered to an adult usually in a dose of approximately 10 to 1,000 mg, preferably approximately 50 to 500 mg, per day depending on the disease, condition and age of the patient.

The compound of the present invention may be formulated into various forms such as a tablet, granules, a powder, a capsule, an injection or a suppository in a conventional manner.

For example, a solid drug for oral administration may be prepared by mixing the active compound(s) with excipient(s) and, if necessary, binder(s), disintegrating agent(s), lubricant(s), colorant(s) and corrigent(s) and formulating the obtained mixture into a tablet, a coated tablet, granules, a powder or a capsule in a conventional manner.

Examples of the excipient are lactose, corn starch, sucrose, glucose, sorbitol and crystalline cellulose. Examples of the binder are polyvinyl alcohol, polyvinyl ether, ethylcellulose, methylcellulose, gum arabic, gum tragacanth, gelatin, shellac wax, hydroxypropylcellulose, hydroxypropylstarch and polyvinylpyrrolidone. Examples of the disintegrating agent are starch, agar, powdery gelatin, crystalline cellulose, calcium carbonate, sodium hydrogencarbonate, calcium citrate, dextrin and pectin. Examples of the lubricant are magnesium stearate, talc, polyethylene glycol, silica and hardened vegetable oils. Pharmaceutically acceptable colorants may be added. Examples of the corrigent are cacao powder, peppermint extract, aromatic acids, peppermint oil, Borneo camphor and cinnamon powder. The tablet or granules thus prepared may be optionally coated with an appropriate material such as sugar or gelatin.

A hypodermical, intramuscular or intravenous injection may be prepared by adding desired pH adjustor(s), solubilizer(s), suspending agent(s), buffer(s), stabilizer(s) and preservative(s) to the active compound(s) and treating the mixture in a conventional manner.

Typical formulations of the compounds of the present invention will now be given.

| Formulation Example 1: Tablet | |
|---|---|
| compound A | 5 g |
| corn starch | 10 g |
| refined sugar | 20 g |
| carboxymethylcellulose calcium | 10 g |
| microcrystalline cellulose | 40 g |
| polyvinylpyrrolidone | 5 g |
| talc | 10 g |
| total | 100 g |

The compound A was dissolved in acetone, adsorbed by microcrystalline cellulose and dried. Corn starch, refined sugar and carboxymethylcellulose calcium were added thereto and then an aqueous solution of polyvinylpyrrolidone was added thereto as a binder. The mixture thus obtained was formulated into granules in a conventional manner. Talc was added to the granules and the mixture was formulated into tablets each weighing 100 mg.

| Formulation Example 2: Capsule | |
|---|---|
| compound B | 5 g |

| Formulation Example 2: Capsule | |
|---|---|
| microcrystalline cellulose | 80 g |
| corn starch | 20 g |
| lactose | 22 g |
| polyvinylpyrrolidone | 3 g |
| total | 130 g |

The ingredients as shown above were formulated into granules in a conventional manner and packed in gelatin hard capsules.

| Formulation Example 3: Powder | |
|---|---|
| compound C | 50 g |
| microcrystalline cellulose | 400 g |
| corn starch | 550 g |
| total | 1,000 g |

The compound C was dissolved in acetone, adsorbed by microcrystalline cellulose and dried. Corn starch was added thereto and the mixture was formulated into a powder in a conventional manner.

| Formulation Example 4: Injection | |
|---|---|
| compound D | 10 g |
| Nikkol HCO-60 | 37 g |
| sesame oil | 2 g |
| sodium chloride | 9 g |
| propylene glycol | 40 g |
| phosphate buffer solution (0.1M, pH 6.0) | 100 ml |
| distilled water q.s. to | 1,000 ml |

The compound D, Nikkol HCO-60, sesame oil and a half amount of the propylene glycol were mixed together and heated to approximately 80° C. for dissolution. Phosphate buffer solution, sodium chloride and the residual propylene glycol previously dissolved in distilled water and heated to approximately 80° C. were added thereto to give an aqueous solution of 1,000 ml in total volume. 1 ml portions of the aqueous solution were poured into ampuls, which were then sealed and sterilized by heating.

Examples of the preparation of the compounds of the present invention will be given for reference.

The embodiments of the invention in which an exclusive property or privilege is claimed are defined as follows:

1. A method of treating a patient to obtain an antiplatelet effect, which comprises administering to a patient requiring such treatment, a therapeutically effective amount of a quinone derivative of the formula:

in which A is a group of the formula:

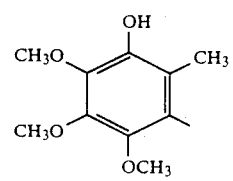

in which n is 2 or 3, or a pharmaceutically acceptable salt thereof, in combination with a pharmaceutically acceptable carrier.

* * * * *